United States Patent
Wittenberger et al.

(10) Patent No.: US 6,575,933 B1
(45) Date of Patent: Jun. 10, 2003

(54) MECHANICAL SUPPORT FOR AN EXPANDABLE MEMBRANE

(75) Inventors: Dan Wittenberger, Pierrefonds (CA); Claudia Lueckge, Pierrefonds (CA); Robert Martin, Poughkeepsie, NY (US); Sean Carroll, Beaconsfield (CA); Leonilda Capuano, Montreal (CA); Margaret Yoklavich, San Jose, CA (US)

(73) Assignee: CryoCath Technologies Inc., Kirkland (CA)

( * ) Notice: Subject to any disclaimer, the term of this patent is extended or adjusted under 35 U.S.C. 154(b) by 0 days.

(21) Appl. No.: 09/491,239

(22) Filed: Jan. 25, 2000

Related U.S. Application Data (63) Continuation-in-part of application No. 09/201,068, filed on Nov. 30, 1998.

(51) Int. Cl.⁷ .............................................. A61M 29/00
(52) U.S. Cl. .................. 604/101.02; 604/509; 128/898; 606/20; 607/96
(58) Field of Search ................ 604/103.09, 43, 604/101.02, 96.01, 20–26, 500, 509, 104–106, 915, 919, 920; 606/191–200, 20–22; 607/96, 104–107, 113; 128/898

(56) References Cited

U.S. PATENT DOCUMENTS

| | | | |
|---|---|---|---|
| 4,572,186 A | * | 2/1986 | Gould et al. ................ 128/341 |
| 4,685,458 A | | 8/1987 | Leckrone ................. 128/303.1 |
| 4,709,698 A | | 12/1987 | Johnston et al. ........ 128/303.12 |
| 4,748,982 A | | 6/1988 | Horzewski et al. .......... 128/344 |
| 4,754,752 A | | 7/1988 | Ginsburg et al. ....... 128/303.12 |
| 4,771,777 A | | 9/1988 | Horzewski et al. .......... 128/344 |
| 4,860,744 A | | 8/1989 | Johnson et al. .......... 128/303.1 |
| 4,924,863 A | | 5/1990 | Sterzer ........................ 606/27 |
| 4,998,933 A | | 3/1991 | Eggers et al. .................. 606/41 |
| 5,078,713 A | | 1/1992 | Varney ......................... 606/23 |
| 5,108,390 A | | 4/1992 | Potocky et al. ............... 606/21 |
| 5,114,423 A | | 5/1992 | Kasprzyk et al. .............. 606/27 |
| 5,139,496 A | | 8/1992 | Hed ............................ 606/23 |
| 5,143,093 A | * | 9/1992 | Sahota ........................ 128/898 |
| 5,147,355 A | | 9/1992 | Friedman et al. ............. 606/23 |
| 5,195,965 A | * | 3/1993 | Shantha ....................... 604/54 |
| 5,275,595 A | | 1/1994 | Dobak, III ................... 606/23 |

(List continued on next page.)

FOREIGN PATENT DOCUMENTS

| | | |
|---|---|---|
| WO | WO 91/05528 | 5/1991 |
| WO | WO 98/38934 | 9/1998 |
| WO | WO 00/47118 | 8/2000 |
| WO | WO 00/54684 | 9/2000 |

*Primary Examiner*—Brian L. Casler
*Assistant Examiner*—Jennifer Maynard
(74) *Attorney, Agent, or Firm*—Christopher & Weisberg, P.A.

(57) ABSTRACT

A medical implement that employs a mechanically supported expandable element. In one embodiment, the mechanically supported expandable element is a balloon. In another embodiment, the mechanically supported expandable membrane is a balloon disposed within a cryogenic catheter usable to treat tissue. A variety of illustrative mechanical support schemes are possible.

4 Claims, 6 Drawing Sheets

U.S. PATENT DOCUMENTS

| | | | | |
|---|---|---|---|---|
| 5,281,215 A | | 1/1994 | Milder | 606/20 |
| 5,342,304 A | * | 8/1994 | Tacklind et al. | 604/99 |
| 5,370,608 A | | 12/1994 | Sahota et al. | 604/20 |
| 5,403,309 A | | 4/1995 | Coleman et al. | 606/20 |
| 5,417,653 A | | 5/1995 | Sahota et al. | 604/20 |
| 5,417,689 A | | 5/1995 | Fine | 606/41 |
| 5,419,760 A | | 5/1995 | Narciso, Jr. | 604/8 |
| 5,452,582 A | | 9/1995 | Longsworth | 62/51.2 |
| 5,527,282 A | | 6/1996 | Segal | 604/104 |
| 5,531,742 A | | 7/1996 | Barken | 606/21 |
| 5,624,392 A | * | 4/1997 | Saab | 604/43 |
| 5,667,505 A | | 9/1997 | Straus | 606/24 |
| 5,695,469 A | | 12/1997 | Segal | 604/104 |
| 5,704,913 A | * | 1/1998 | Abele et al. | 604/101 |
| 5,716,353 A | | 2/1998 | Matsuura et al. | 606/22 |
| 5,720,717 A | * | 2/1998 | D'Andrea | 604/21 |
| 5,755,708 A | | 5/1998 | Segal | 604/109 |
| 5,772,681 A | | 6/1998 | Leoni | 606/192 |
| 5,775,338 A | | 7/1998 | Hastings | 128/898 |
| 5,797,948 A | * | 8/1998 | Dunham | 606/94 |
| 5,800,486 A | | 9/1998 | Thome et al. | 607/105 |
| 5,800,487 A | | 9/1998 | Mikus et al. | 607/105 |
| 5,800,488 A | | 9/1998 | Crockett | 607/105 |
| 5,807,391 A | | 9/1998 | Wijkamp | 606/23 |
| 5,833,685 A | | 11/1998 | Tortal et al. | 606/23 |
| 5,836,957 A | * | 11/1998 | Schulz et al. | 606/159 |
| 5,860,970 A | | 1/1999 | Goddard et al. | 606/23 |
| 5,868,735 A | * | 2/1999 | Lafontaine | 606/21 |
| 5,971,979 A | * | 10/1999 | Joye et al. | 606/21 |
| 6,059,752 A | | 5/2000 | Segal | 604/107 |
| 6,059,812 A | | 5/2000 | Clerc et al. | 606/198 |
| 6,149,574 A | * | 11/2000 | Trauthen et al. | 600/3 |
| 6,217,585 B1 | * | 4/2001 | Houser et al. | 606/108 |
| 6,312,407 B1 | * | 11/2001 | Zadno-Azizi et al. | 604/103.03 |

* cited by examiner

MECHANICAL SUPPORT FOR AN EXPANDABLE MEMBRANE

CROSS REFERENCE TO RELATED APPLICATIONS

This application is a continuation-in-part of U.S. patent application Ser. No. 09/201,068, filed Nov. 30, 1998.

STATEMENT REGARDING FEDERALLY FUNDED RESEARCH

Not Applicable.

FIELD OF THE INVENTION

The present invention relates generally to medical implements, and more particularly to a medical implement that employs a mechanically supported expandable membrane as part of the implement.

BACKGROUND OF THE INVENTION

It is well known to perform an angioplasty procedure to open an arterial vessel that, for example, is occluded due to arteriosclerosis. Typically, a balloon catheter is inserted into a patient's arterial network and manipulated to the occluded region of the vessel which is often proximate the heart. The balloon portion of the catheter is inflated so as to compress the arterial plaque against the vessel walls. The luminal area of the vessel is thereby increased, allowing more blood to flow through the vessel.

While the angioplasty procedure may initially be successful, a significant percentage of patients experience restenosis of the treated area. That is, the opened region of the vessel gradually recloses in a relatively short amount of time, such as about six months. Although the exact mechanism is not understood, restenosis is generally believed to involve platelet aggregation, thrombus formation, and smooth cell migration and proliferation, either singly or in combination. However it occurs, restenosis ultimately negates the benefits achieved by the angioplasty procedure.

In order to prevent mechanical recoil of the vessel wall following angioplasty, as well as to mitigate the effects of restenosis, a stent may be implanted in the opened region of the vessel after the angioplasty procedure. As known to one of ordinary skill in the art, a typical stent has a generally cylindrical shape to conform to the vessel and can be formed from a wire mesh. However, stents may irritate the vessel wall. Further, in some patients stents are believed to be the cause of rapid tissue growth, or intimal hyperplasia, through openings in the stent walls.

Some prior art devices and methods have called for the use of cooling treatment to prevent restenosis. For example, U.S. Pat. No. 5,417,653 briefly discusses a method of inhibiting restenosis by reducing the temperature of tissue at a treatment site by infusion of a fluid such as n-saline. However, fluid infusion as a treatment method may be inaccurate in targeting desired tissue and may introduce unwanted fluids or pathogens into a patient.

It would, therefore, be desirable to provide a device capable of treating a vessel region to prevent restenosis without the disadvantages highlighted above.

SUMMARY OF THE INVENTION

The present invention provides a medical implement comprising an expandable membrane with an element disposed within a lumen formed by the membrane. One embodiment of such an implement may be a mechanically supported balloon used as part of a catheter. In yet another embodiment, a mechanically supported balloon is incorporated as part of a cryogenic catheter that delivers cryogenic energy to minimize restenosis of a dilated region of a treated blood vessel. Cryogenic fluid is delivered to the expanded balloon and thereby cools the tissue in contact with an outer side of the balloon. Mechanical support for the balloon may, for example, be provided by a helical shape memory coil or a series of shape memory sections that deform against an inner side of the balloon, thus inflating the balloon. A variety of alternate mechanical support schemes may be employed to reach a similar result.

BRIEF DESCRIPTION OF THE DRAWINGS

The invention will be more fully understood from the following detailed description taken in conjunction with the accompanying drawings, in which.

DETAILED DESCRIPTION OF THE INVENTION

The present invention provides a mechanically supported expandable membrane. The membrane may be a balloon with an element disposed within its lumen. The element may include one or more of a number of support schemes, some of which are discussed in the illustrative embodiments below.

A mechanically supported balloon may, for instance, be used as part of a cryogenic catheter used to treat a vessel with cryogenic energy to prevent restenosis or to selectively ablate tissue. In general, such a catheter is inserted into the patient's vascular network and manipulated to a treatment site. The catheter is then expanded and energized so as to cool the contacted tissue at the treatment site to a predetermined temperature for a desired amount of time. It is understood that a variety of cryogenic catheter configurations can be used to apply cryogenic energy levels to the treatment site. If desired, such a medical implement may also employ other means of treating tissue, such as RF energy or other method of heating tissue, either in combination with cryotherapy or as a separate treatment mode.

Typically, an occluded region of the vessel is dilated by means of a percutaneous transluminal coronary angioplasty (PTCA) which includes the use of a balloon catheter. The catheter is inserted into the patient, in the groin area for example, and manipulated to the occluded region of the patient's artery. The balloon is then inflated so as to increase the luminal area of the vessel and thereby increase blood flow through the artery. A stent, which is expandable by the balloon catheter, can be placed within the treated area to prevent mechanical recoil of the vessel wall.

In accordance with the present invention, an expandable balloon is provided wherein a mechanical support element is disposed in the lumen of the balloon. When the element is in a second state, i.e., expanded, the element contacts an inner side of the balloon and thus the balloon expands. The expanded balloon provides a region that contacts an inner lumen of a biological vessel or cavity, thereby allowing for cryogenic or hyperthermal treatment in irregularly shaped areas of a patient. Further, the mechanical support afforded the balloon allows for balloon expansion when the pressure outside the balloon is greater than the pressure inside the balloon.

Figure 1:
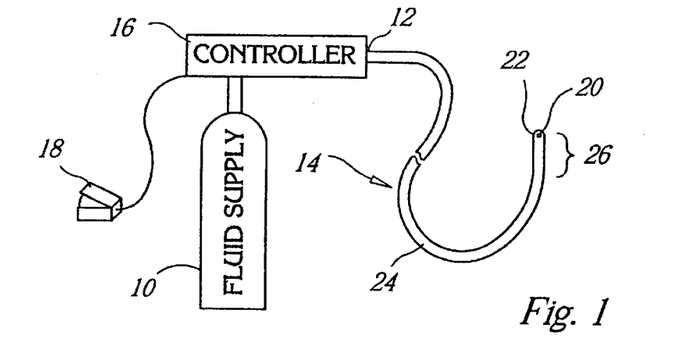
FIG. 1 is a schematic diagram of a cryosurgical system including a catheter for use in conjunction with the present invention.

FIG. 1 is a schematic illustration of an exemplary cryosurgical system for use with the device of the present invention. The system includes a supply of cryogenic or cooling fluid 10 in communication with the proximal end 12 of a flexible catheter 14. A fluid controller 16 is interposed or in-line between the cryogenic fluid supply 10 and the catheter 14 for regulating the flow of cryogenic fluid into the catheter in response to a controller command. Controller commands can include programmed instructions, sensor signals, and manual user input. For example, the fluid controller 16 can be programmed or configured to increase and decrease the pressure of the fluid by predetermined pressure increments over predetermined time intervals.

In another exemplary embodiment, the fluid controller 16 can be responsive to input from a foot pedal 18 to permit flow of the cryogenic fluid into the catheter 14. One or more temperature sensors 20 in electrical communication with the controller 16 can be provided to regulate or terminate the flow of cryogenic fluid into the catheter 14 when a predetermined temperature at a selected point or points on or within the catheter is/are obtained. For example, a temperature sensor can be placed at a point proximate the distal end 22 of the catheter and other temperature sensors 20 can be placed at spaced intervals between the distal end of the catheter and another point that is between the distal end and the proximal end.

The catheter 14 includes a flexible member 24 having a thermally-transmissive region 26 and a fluid path through the flexible member to the thermally-transmissive region. A fluid path is also provided from the thermally-transmissive region to a point external to the catheter, such as the proximal end 12. Exemplary fluid paths include one or more channels defined by the flexible member 24, and/or by one or more additional flexible members that are internal to the first flexible member 24. Also, even though many materials and structures can be thermally conductive or thermally transmissive if chilled to a very low temperature and/or cold soaked, as used herein, a "thermally-transmissive region" is intended to broadly encompass any structure or region of the catheter 14 that readily conducts heat.

Furthermore, while the thermally-transmissive region 26 can include a single, continuous, and uninterrupted surface or structure, it can also include multiple, discrete, thermally-transmissive structures that collectively define a thermally-transmissive region that is elongate or linear. Depending on the ability of the cryogenic system, or portions thereof, to handle given thermal loads, the ablation of an elongate tissue path can be performed in a single or multiple cycle process without having to relocate the catheter one or more times or drag it across tissue.

In some embodiments, the thermally-transmissive region 26 of the catheter 14 is deformable. An exemplary deformation is from a linear configuration to an arcuate configuration and is accomplished using mechanical and/or electrical devices known to those skilled in the art. For example, a wall portion of the flexible member 24 can include a metal braid to make the catheter torqueable for overall catheter steering and placement. Additionally, a cord, wire or cable can be incorporated with, or inserted into, the catheter for deformation of the thermally transmissive region 26. Further, a balloon can be incorporated into the thermally transmissive region 26 such that the catheter can dilate the occluded region of the vessel as well as treat the dilated region with cryogenic energy.

Figure 2:
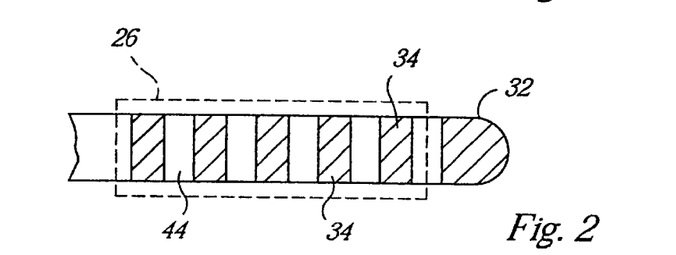
FIG. 2 is a side view of a tip region of the catheter of FIG. 1.
Figure 3:
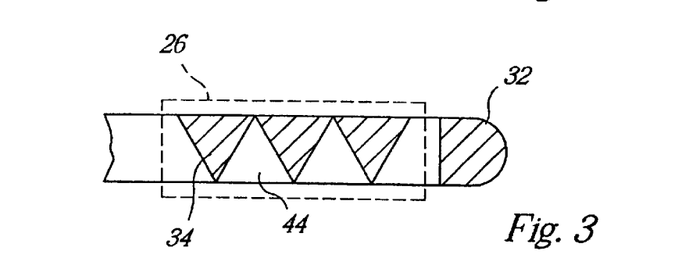
FIG. 3 is a side view of an alternative embodiment of the catheter tip region of the FIG. 2.
Figures 4, 5:
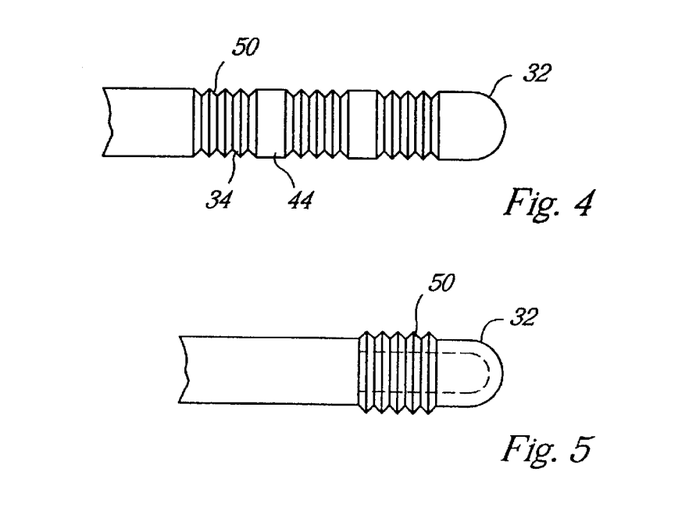
FIG. 4 is a side view of another embodiment of the catheter tip region of FIG. 1.
FIG. 5 is a side view of a further embodiment of the catheter tip region of FIG. 1.

In other embodiments, such as those shown in FIGS. 2, 3 and 4 for example, the catheter, or portions thereof, have two or more thermally-transmissive segments in a spaced-apart relationship. Each of the illustrated catheters includes a closed tip 32 that can include a thermally-transmissive material.

With respect to the embodiments shown in both FIGS. 2 and 3, the thermally-transmissive elements 34 are substantially rigid and are separated and/or joined by a flexible material 44. However, in other embodiments the thermally-transmissive elements 34 are flexible and are interdigitated with either rigid or flexible segments. FIG. 4, for example, illustrates an embodiment of the cryogenic catheter having three thermally-transmissive elements 34 that are flexible. The flexibility is provided by a folded or bellows-like structure 50. In addition to being shapable, a metal bellows can have enough stiffness to retain a selected shape after a deforming or bending step.

Instead of, or in addition to, flexible, thermally-transmissive elements 34 and/or flexible material 44 between elements, the distal tip 32 (or a portion thereof) can be deformable. For example, FIG. 5 illustrates a tip 32 having thermally-transmissive, flexible, bellows 50.

Figure 6:
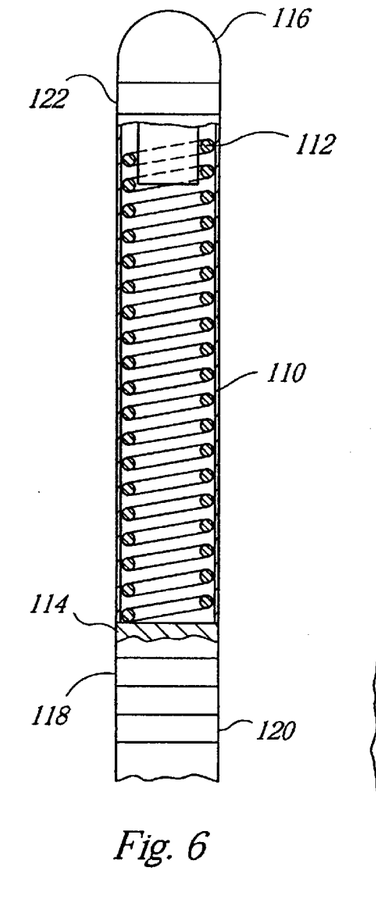
FIG. 6 is a partial cutaway of a side view of yet another embodiment of the catheter of FIG. 1.

FIG. 6 illustrates another embodiment of a cryogenic cooling structure that includes a surface or wall 110 including a polymer or elastomer that is thin enough to permit thermal transfer. For example, polyamide, PET, or PTFE having a thickness of a typical angioplasty balloon or less (below 0.006 inches) provides acceptable thermal transfer. However, the thinness of the wall 110 allows it to readily collapse or otherwise deform under vacuum or near vacuum conditions applied to evacuate fluid/gas from the structure. Accordingly, the structure is provided with one or more supporting elements 112 such as a spring. It should be noted that a variety of other supporting elements may be used to achieve the same goal and, as such, further support embodiments are discussed below. The cooling structure is illustrated in association with a catheter 114 having a closed distal tip 116 and mono or bipolar ECG rings 118, 120, 122. The thermally-transmissive region is approximately 30 mm in length and is effective for thermal transfer over its entire circumference. However, the thermally-transmissive region can be confined to specific region(s) of the device's circumference.

It is understood that other types of cryogenic catheters having differing types of distal tips can be used. Further exemplary catheters that can be used in conjunction with the method of the present invention are shown and described in co-pending and commonly assigned U.S. patent application Ser. No. 08/893,825, filed on Jul. 11, 1997, incorporated herein by reference.

In an exemplary procedure, a cryogenic catheter having a ten millimeter cooling segment with a five French diameter, which can be obtained from CryoCath Technologies Inc. of St. Laurent, Quebec, Canada, is inserted into the patient's arterial network. The catheter is then manipulated to a region of the vessel that is dilated using a conventional PTCA, for example. A distal tip of the catheter is positioned so as to contact the dilated region of the vessel. The catheter is then energized so as to cool the tissue in contact with the distal tip of the catheter.

Cryogenic energy can be applied to the treatment site in a wide range of temperatures and for various time intervals depending on the desired effect. By varying treatment parameters, treated tissue may be ablated or left viable to a desired degree. For example, energy can be applied such that the tissue temperature is constant or it can vary. Further, energy can be applied for one or more predetermined time intervals at the same or different temperatures. The time intervals can vary as well, so as to achieve a desired level of cryogenic treatment for the target tissue. Also, certain areas of the treatment site may be cooled to a greater or lesser extent than surrounding target tissue.

In general, the tissue at the treatment site, e.g., the region of the vessel or vessel opening in need of dilation, is cooled to a temperature in the range from about zero degrees Celsius to about minus one hundred and twenty degrees Celsius for a period of time ranging from about ten seconds to about sixty minutes. It is understood that as tissue is cooled to more extreme temperatures the duration of the treatment can be decreased. In one embodiment, the treatment site is cooled to a temperature of about minus fifty degrees Celsius for about two minutes. Of course, if tissue ablation is the desired result, the treatment temperature may be further depressed and/or the duration of the treatment may be increased beyond the treatment parameters disclosed above.

In contrast with heat and radiation tissue treatments, the application of cryogenic energy produces less damage to the arterial wall structure. The damage reduction occurs because a freeze injury does not significantly alter the collagen structure as compared with the application of heat. Further, a freeze injury does not significantly reduce the reproductive/repair capability of the living tissue as compared with radiation treatments.

Figure 7:
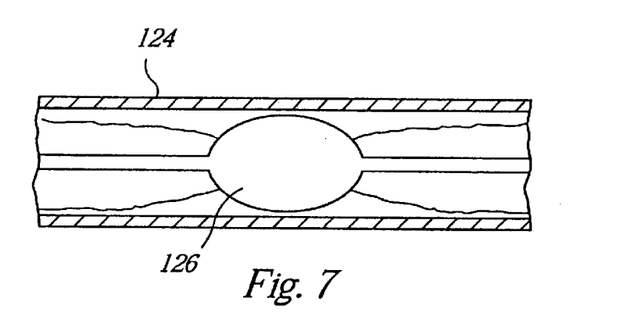
FIG. 7 is a pictorial diagram of a balloon catheter inflated within an artery.

As shown in FIG. 7, cryogenic energy can be applied to a vessel region 124 dilated with a balloon catheter 126, wherein the balloon catheter is infused with a cryogenic fluid and maintained in contact with tissue for a period of time as described above. Although this procedure can have a restenosis effect, a surgeon may also wish to implant a stent. Thus, in another exemplary procedure, a balloon dilated region of a vessel is treated with cryogenic energy prior to implantation of a vascular stent. By treating the tissue with cryogenic energy, rapid tissue growth or so-called remodeling commonly associated with implanted stents is believed to be reduced or substantially prevented.

Figure 8:
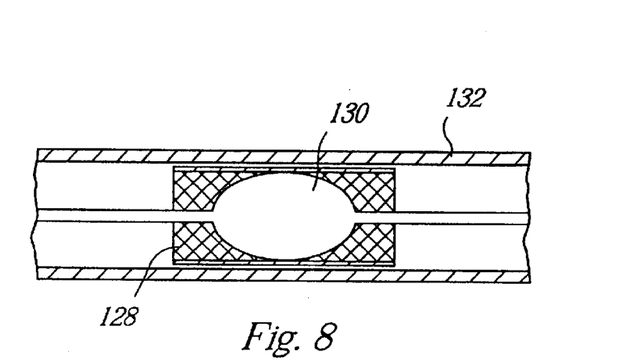
FIG. 8 is a pictorial diagram of a stent being expanded by a balloon catheter.

As shown in FIG. 8, a stent 128 can be expanded by a cryoballoon catheter following the cryo-treatment of a vessel 132 or simultaneous with the cryo-treatment. Also, the stent can be expanded and then cryo-treatment can begin.

Figure 9:
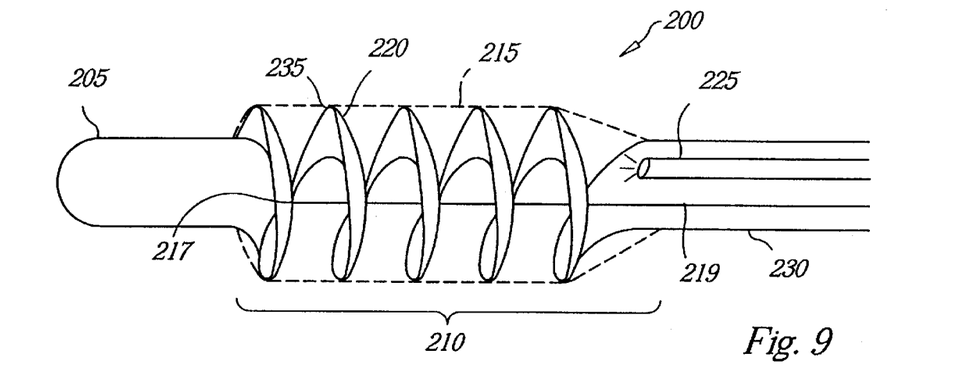
FIG. 9 is a side view of a mechanically supported expandable membrane where the mechanical support element is a helical coil.

Referring now to FIG. 9, a balloon catheter 200 has a proximal segment 230 distal to a proximal end (not shown). The proximal segment 230 has running through it a conduit 225 for delivering cryogenic fluid to a distal side of the proximal segment 230. The proximal segment 230 also has therein a pull wire 219 that terminates at a connection point 217, thereby fixedly attaching the pull wire 219 to a helical coil 220 (discussed below). The proximal segment 230 is adjacent to a balloon region 210 and is sealed at its distal end to the balloon membrane 230. The distal side of the balloon membrane 230 is sealed on its distal side to the distal segment 205. The seals between the balloon membrane 230 and the distal end of the proximal segment 230, and between the balloon membrane 230 and the proximal end of the distal segment 205, prevent both the entry or exit of fluids into or from the catheter 200.

It should be noted that the balloon membrane 215 is shown in an expanded condition. Contacting an inner wall 235 of the balloon membrane 215 is a helical coil 220. The helical coil 220 is shown in a second state, i.e., expanded, such that the diameter of at least a portion of the helical coil 220 is greater than the diameter of the same portion when the helical coil 220 is in a first state, i.e., relaxed. The expansion of the helical coil 220 may, for example, be effectuated by a simple actuation at the proximal end (not shown) of the balloon catheter 200, i.e., a lever or switch connected to the pull wire 219, or by constructing the helical coil 220 of shape-memory material, or a combination thereof. A change in temperature may also be used to expand the helical coil 220.

In operation, cryogenic fluid from the conduit 225 enters balloon membrane 215 when balloon membrane 215 is in the expanded condition. The cryogenic fluid expands upon entering the balloon membrane 215, thereby creating a cooling effect. Tissue in contact with the balloon membrane 215 is cooled to the desired temperature. Other methods of cooling using a fluid flowing through a balloon membrane such as balloon membrane 215 are readily evident, such as sustaining a fluid flow rate through the balloon membrane 215 sufficient to achieve the desired cooling of tissue in contact with the balloon membrane 215.

Figure 10:
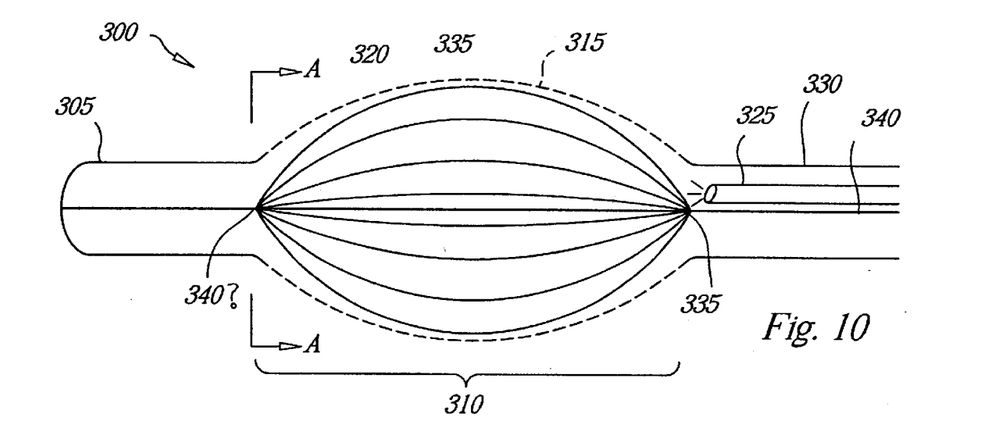
FIG. 10 is a side view of a mechanically supported expandable membrane where the mechanical support element is a plurality of radially spaced members.

Another embodiment that demonstrates the use of a mechanically supported expandable membrane is seen in FIG. 10. As discussed in relation to FIG. 9, a balloon catheter 300 has a proximal segment 330 leading to a proximal end (not shown) and a distal segment 305. The proximal segment 330 has running through it a conduit 325 for delivering cryogenic fluid to a distal end of the proximal segment 330. The balloon region 310 includes a balloon membrane 315 sealed to the distal segment 305 and sealed to the proximal segment 330 so as to prevent the both the entry or exit of fluids into or from the catheter 300. The balloon membrane 315 is shown in an expanded condition.

Contacting an inner wall 335 of the balloon membrane 315 is a plurality of radially spaced apart members 320. The plurality of members 320 converge proximally at junction 335 and distally at junction 340. Changing the distance between junction 335 and junction 340 allows for selectable transitionability between a first state and a second state. In FIG. 10, the plurality of members 320 is shown in a second state, i.e., expanded, such that the diameter of at least a portion of the plurality of members 320 is greater than the diameter of the same portion when the plurality of members 320 is in a first state, i.e., relaxed.

Figure 10A:
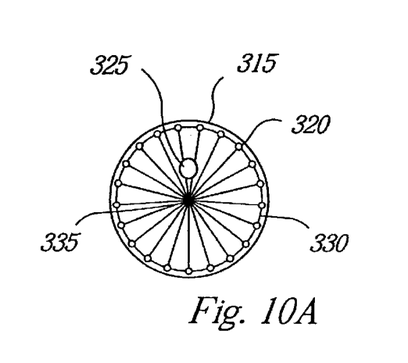
FIG. 10A is a cross-sectional view taken along section A—A of the implement of FIG. 10, where the balloon is not expanded.
Figure 10B:
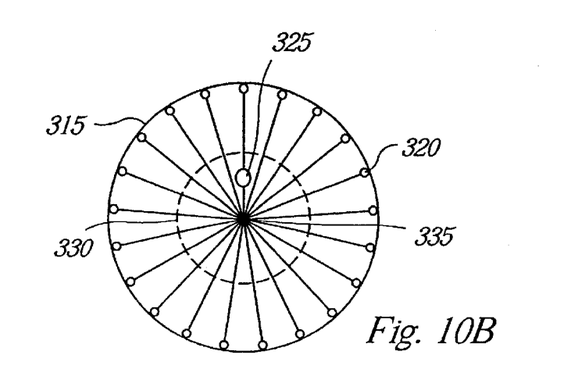
FIG. 10B is a cross-sectional view taken along section A—A of the implement of FIG. 10, where the balloon is expanded.

FIGS. 10A and 10B illustrate the differences between the first state and the second state. In FIG. 10A, the balloon membrane 315 is unexpanded and the plurality of members 320 is in the first state. Comparing FIG. 10A to FIG. 10B, in FIG. 10B the balloon element 315 has expanded, as is dictated by the configuration of the plurality of members 320 in the second state. It should be noted that in this expanded condition, cryogenic fluid is able to flow from the conduit 325 into the lumen of the balloon member 315, thus effecting cooling of tissue contacting the balloon member 315.

Figure 11A:
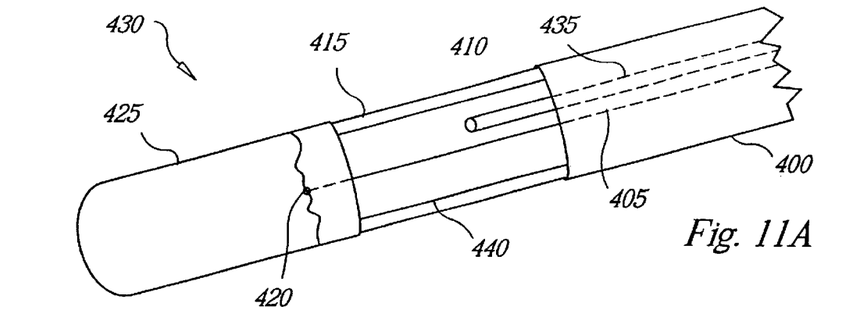
FIG. 11A is a pictorial diagram of another embodiment of a mechancially supported expandable balloon, shown with the balloon in an unexpanded state.
Figure 11B:
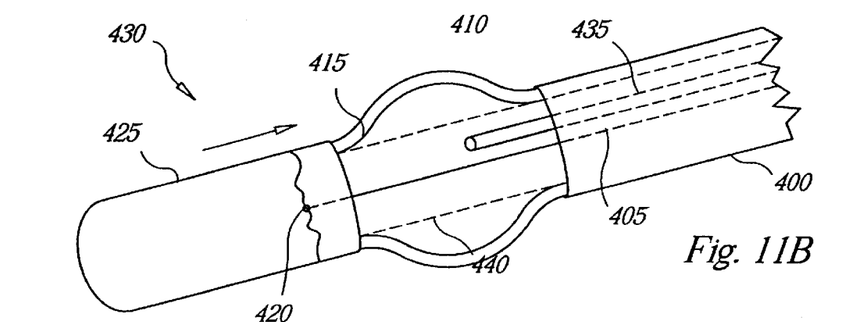
FIG. 11B is a pictorial diagram of the implement of FIG. 11A, shown in its expanded state.

In FIGS. 11A and 11B, the element within the lumen of the expandable membrane is deformable wire mesh that is expanded when either a proximal segment of a catheter is moved towards a distal segment, or when a distal segment is moved towards a proximal segment. The expanded mesh region defines a cooling region should cryogenic fluid be circulated through the catheter.

Referring to FIG. 11A, a proximal segment 400 has running through it a pull wire 405 and a fluid conduit 435. The pull wire 405 exits the proximal segment 400 at a distal end and continues through the mesh region 410 and terminates within the distal segment 425 at a connection point 420. The connection point 420 may be attached to the distal segment 425 such that when the connection point 420 moves either proximally or distally, the distal segment 425 moves with it. The mesh region 410 has on its inner side, i.e., within its lumen, medial segment 440, within which fluid conduit 435 terminates. An outer side of the mesh region 410, is surrounded by the balloon membrane 415, balloon membrane 415 being sealed at a proximal end to the proximal segment 400 and at a distal end to the distal segment 425 such that fluids are incapable of exiting or entering the catheter 430.

FIG. 11B shows the catheter 430 of FIG. 11A with the balloon membrane 415 in an expanded state. Such a state is brought about by reducing the distance between the connection point 420 and the proximal segment 400. The reduction in distance, for example, may be caused by actuating a lever or switch located at a proximal handle (not shown) of the catheter 430 such that a pull wire 405 is drawn towards the proximal handle. When the connection point 430 moves towards the proximal handle, the mesh region 410 deforms outwardly, thus achieving the desired expansion of the balloon membrane 415. As mentioned above, one could achieve a substantially similar result by moving the proximal segment 400 towards the connection point 430. When the catheter 430 is in this expanded state, cooling fluid preferentially flows through fluid conduit 435 into the lumen of mesh region 410, thereby allowing cryogenic treatment to occur.

Figure 12A:
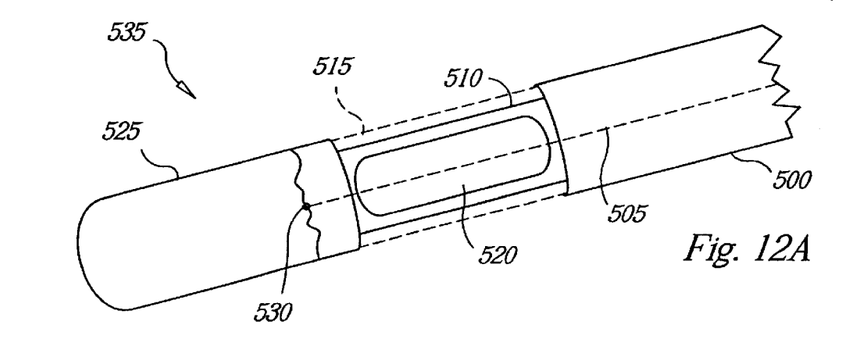
FIG. 12A is a pictorial diagram of yet another possible embodiment of an expandable balloon with mechanical support, shown with the balloon in an unexpanded state.

FIG. 12A demonstrates yet another embodiment of a mechanically supported expandable balloon. In this embodiment, a proximal segment 500 has running through it a pull wire 505. The pull wire 505 exits the proximal segment 500 at a distal end, continues through strut region 510, enters a proximal end of the distal segment 525, and terminates at a connection point 530. The connection point 530 may be attached to the distal segment 525 such that when the connection point 530 moves either proximally or distally, the distal segment 525 moves with it. The strut region 510 is surrounded by the balloon membrane 515, balloon membrane 515 being sealed at a proximal end to the proximal segment 500 and at a distal end to the distal segment 525 such that fluids are incapable of exiting or entering the catheter 430.

Figure 12B:
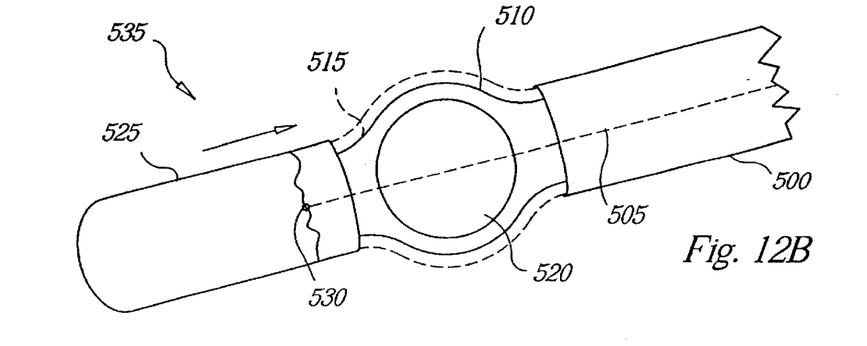
FIG. 12B shows the implement of FIG. 12A in its expanded state.

FIG. 12B shows the catheter 535 of FIG. 12A with the balloon membrane 515 in an expanded state. Such a state is brought about by reducing the distance between the connection point 530 and the proximal segment 500. Once again, the reduction in distance, for example, may be caused by actuating a lever or switch located at a proximal handle (not shown) of the catheter 535 such that a pull wire 505 is drawn towards the proximal handle. When the connection point 530 moves toward the proximal handle, the strut region 510 deforms outwardly, thus achieving the desired expansion of the balloon membrane 515. Alternatively, the proximal segment 500 could be moved towards the connection point 530 to achieve a substantially similar result.

Figure 13:
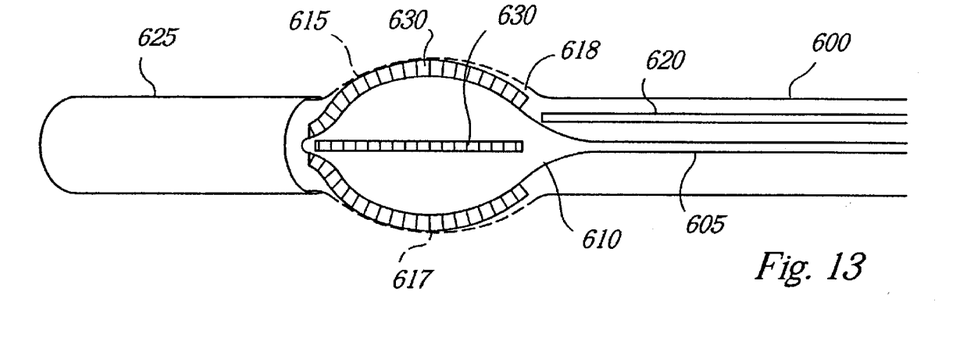
FIG. 13A is a pictorial diagram of another illustrative embodiment of a mechanically supported expandable balloon, where the mechanical support is provided by an inner membrane spaced apart from the balloon.
FIG. 13B is a cross-sectional view of the implement of FIG. 13A shown in its expanded state.

FIG. 13 illustrates another embodiment having a second expandable membrane, such as a balloon, disposed in the lumen of the first expandable membrane. The inner balloon is spaced apart from the expandable membrane by a series of radially spaced members. Thus, when the inner balloon element is expanded, the spacers are forced against the inner wall of the expandable membrane, thereby causing expansion of the membrane.

Specifically, FIG. 13 shows a catheter whose proximal segment 600 preferably includes within it an air supply line 605 and a fluid supply line 620. The air supply line 605 terminates in an inner balloon 610, shown in an expanded condition. It should be noted that air inflation of the inner balloon 610 is merely one of a number of possible expansion methods. The inner balloon 610 has surrounding it a plurality of members 630, spaced radially apart around a longitudinal axis of the inner balloon 610. In this expanded condition, the members 630 contact an inner side 617 of an outer balloon 615. Cryogenic fluid may preferably be introduced into the space 618 created in this arrangement between the inner balloon 610 and the outer balloon 615 through fluid supply line 620.

Figure 14:
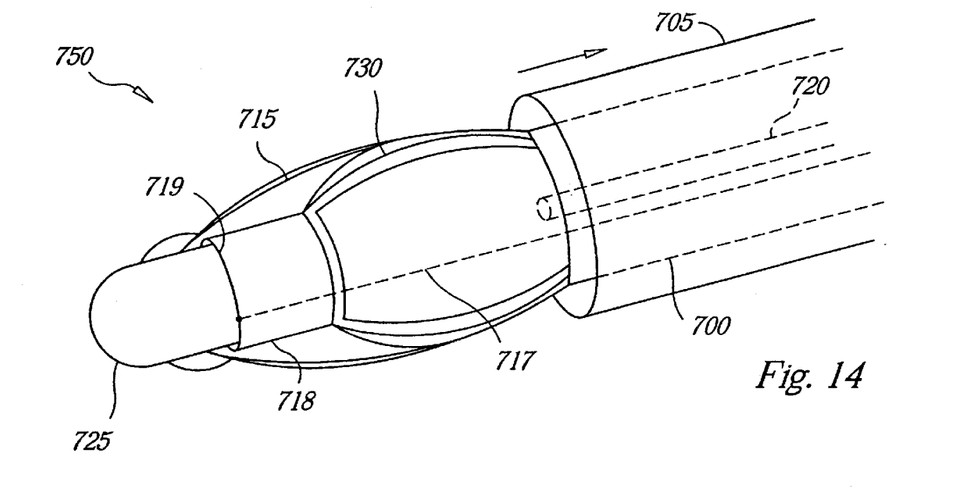
FIG. 14 is a pictorial diagram of yet another embodiment of a mechanically supported expandable balloon, employing as part of its support element a sleeve assembly.

Turning to another illustrative embodiment, in FIG. 14 a catheter 750 includes a sleeve 705 slidably engaged with a proximal segment 700. Running through the proximal segment 700 is a fluid supply line 720 and a pull wire 717. Pull wire 717 terminates at a connection point 719 on a slotted tube 718. The slotted tube 718 is shown being attached to a pair of deformable struts 730 at its proximal end. Further, a balloon membrane 715 is sealed at its proximal end to the proximal segment 700 and sealed at its distal end to a distal segment 725 such that fluids are incapable of entering the catheter 750. The balloon membrane 725 is shown in an expanded condition and is mechanically supported by deformable struts 730. In operation, the catheter 750 is guided to a desired treatment location within a patient's body. Once reached, a sleeve 705 is slid proximally, exposing the balloon membrane 715 to the treatment site. The struts 730 are then deformed outwards by pulling the pull wire 717 toward the proximal end of the catheter (not shown) such that slotted tube 718 moves in a proximal direction. Cryogenic fluid then enters the lumen of the balloon membrane 715, such that the desired treatment may be effectuated.

Figure 15:
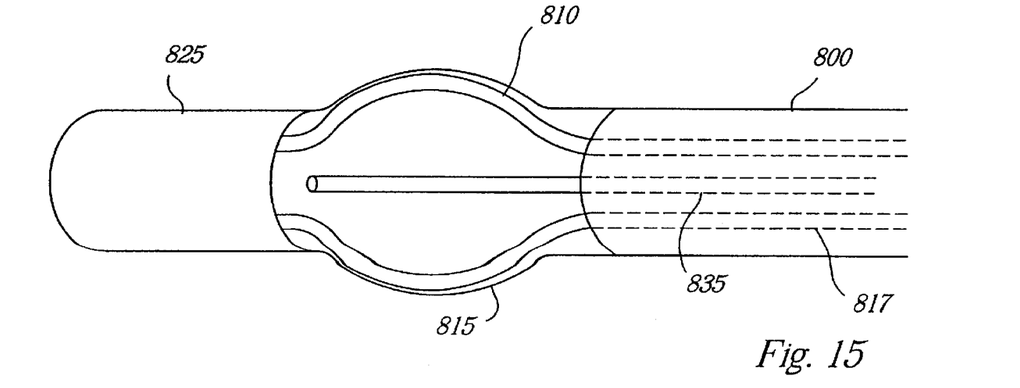
FIG. 15 is a pictorial diagram of a further embodiment of a mechanically supported expandable balloon, employing as part of its support element a push rod that actuates and causes the support element to deform towards the balloon.

Referring now to FIG. 15, a catheter has a proximal segment 800 within which is disposed a push rod 817. A fluid conduit 835 is disposed within the push rod 817. Push rod 817 terminates at a point distal to the proximal segment 800 and separates into at least two flat metal wires 810. The flat metal wires 810 contact an inner surface of a balloon membrane 815 when the balloon membrane 815 is in an expanded condition, as is shown in FIG. 15. The flat metal wires 810 terminate at a proximal end of a distal segment 825 and are biased against the distal segment 825 such that when the push rod 817 is actuated in a distal direction, i.e., a force F is applied in the direction shown in FIG. 15, the flat metal wires 810 deform against the inner surface of the balloon membrane 815, thereby expanding the balloon membrane 815.

Figure 16A:
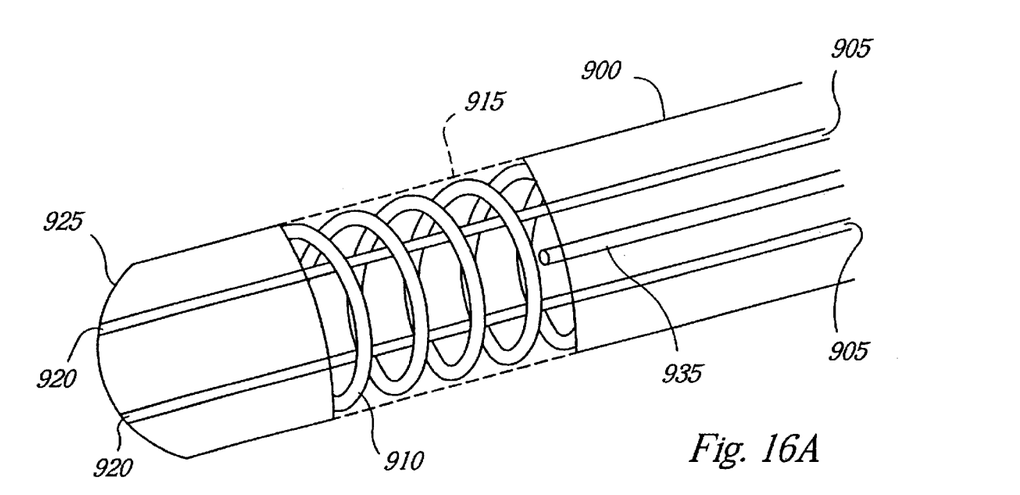
FIG. 16A is pictorial diagram of another embodiment of a mechanically supported expandable balloon, where the mechanical support is provided by an expandable spring.
Figure 16B:
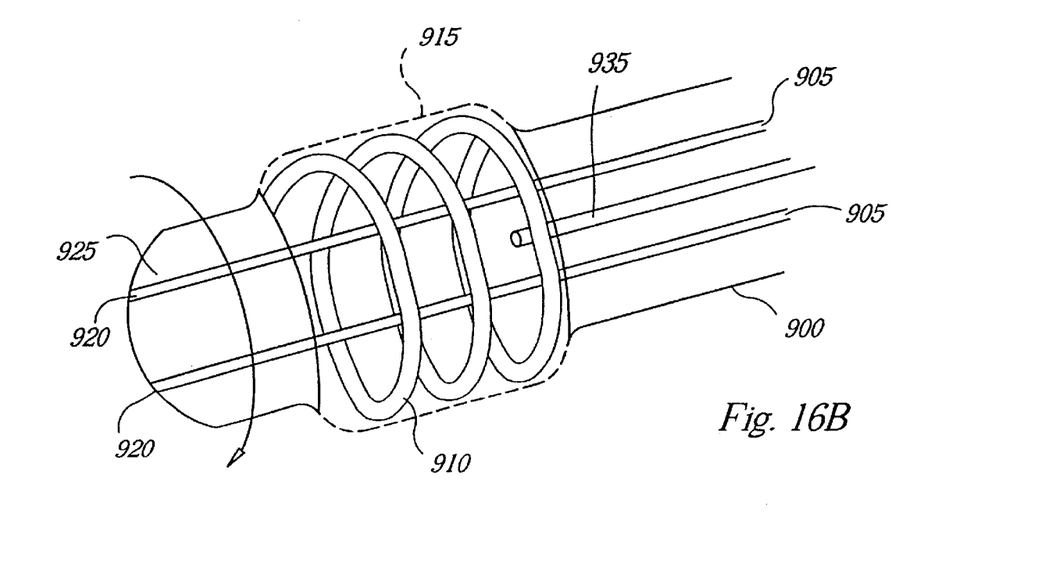
FIG. 16B is a pictorial diagram of the implement of FIG. 16A shown in an expanded state.

Referring now to the catheter tip embodiment illustrated in FIGS. 16A and 16B, a proximal segment 900 has running through it a guide wire system 905 and a fluid conduit 935. The proximal segment 900 is separated from a distal segment 925 by a gap of longitudinal distance D. The guide wire system 905 exits the proximal segment 900, traverses the gap, and terminates in an end of distal segment 925 at connection point 920. Disposed within the gap between proximal segment 900 and distal segment 925 is an expandable spring 910. The expandable spring 910 is connected to the proximal segment 900 at one end and to the distal segment 925 at the other end. The expandable spring 910 has surrounding it an expandable membrane 915.

In operation, a control at a proximal end of the catheter (not shown) imparts a rotation to the distal segment 925 by applying a torque to the guide wire system 905. Thus, as the guide wire system 905 is affixed to distal segment 925 at the connection point 920, when the guide wire system 905 is rotated, so is the distal segment 925. Similarly, as the distal segment 925 is affixed to the expandable spring 910, when the distal segment 925 is rotated, so is the expandable spring 910.

Throughout this procedure, the distance D between the proximal segment 900 and the distal segment 925 remains substantially constant; thus the rotation imparted to the expandable spring 910 serves to increase the profile of the expandable spring 910 in an axial direction instead of in a longitudinal direction. Alternatively, the same result may be achieved by imparting a rotation to the proximal segment 900 or by rotating the expandable spring 910 directly. When the expandable spring 910 is thus expanded, the expandable membrane 915 in contact with the expandable spring 910 is also expanded, thereby allowing for treatment of tissue contacted by expandable membrane 915. As discussed above, cryogenic treatment may be performed, for example, by the expansion of cooling fluid introduced into the lumen of the expandable membrane 915 through the fluid conduit 935.

It should be emphasized that any of the above suggested embodiments may employ as the method of deforming the element shape-memory alloys, changes in element length and/or diameter via physical actuation, temperature changes, or a combination thereof, to accomplish the invention. Further, it should be noted that additional features may be incorporated into the mechanically supported membrane of the invention, such as a deflection mechanism employing one or more pull-wires to enable steering of the catheter, or a plurality of ECG electrode rings spaced longitudinally apart along the catheter to allow for monitoring activity proximate a treatment site. Other types of electrodes may also be incorporated, such as electrodes designed to deliver thermal energy for treatment or ablation. Finally sensors for measuring temperature and other physiologically relevant parameters may by provided as part of the invention.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A medical implement, comprising:
    a first expandable membrane transitionable between a contracted state and an expanded state, the expandable membrane having:
        an outer side and an opposite inner side defining a membrane wall and a lumen; and
        a thermally transmissive region transferring thermal energy between the outer side and the opposite inner side; and a non-inflatable element disposed within the lumen, the non-inflatable element supporting the first expandable membrane, the non-inflatable element being operable to increase the diameter of at least a portion of the non-inflatable element to support the first expandable membrane in the expanded state, wherein the non-inflatable element comprises a second expandable membrane disposed within the lumen defined by the first expandable membrane.

2. A method of dilating and cryogenically treating an occluded region of a vessel, comprising:
    inserting a balloon catheter having a mechanically supported membrane into the occluded region of the vessel;
    inflating the balloon to dilate the occluded region of the vessel; and treating the dilated vessel region with cryogenic energy, including cooling the dilated region of the vessel to a temperature that is between about 0° C. to minus 120° C. degrees Celsius for a period of time greater than about ten seconds; the mechanically supported membrane having a support structure disposed within the balloon capable of maintaining the balloon in an inflated condition when pressure on an outer side is exceeded by pressure on an inner side of the balloon.

3. The method according to claim 2, further including implanting a stent proximate the dilated region of the vessel.

4. The method according to claim 2, further including hyperthermal treatment of the vessel.

* * * * *